United States Patent [19]

Parker

[11] 4,102,338

[45] Jul. 25, 1978

[54] HARDENABLE SHEET MATERIALS

[75] Inventor: Robert Sydney Richard Parker, Little Hallingbury, Near Bishop's Stortford, England

[73] Assignee: National Research Development Corporation, England

[21] Appl. No.: 734,309

[22] Filed: Oct. 20, 1976

Related U.S. Application Data

[63] Continuation of Ser. No. 525,731, Nov. 21, 1974, abandoned.

[30] Foreign Application Priority Data

Nov. 29, 1973 [GB] United Kingdom ............... 55471/73

[51] Int. Cl.² ............................................... A61F 5/04
[52] U.S. Cl. ..................................... 128/90; 428/245; 428/255; 428/259; 428/264; 428/283; 428/304; 428/446
[58] Field of Search ............... 128/90, 91; 260/29.6 H, 260/42.55; 428/245, 252, 264, 283, 304, 446, 507, 522, 539, 255, 259

[56] References Cited

U.S. PATENT DOCUMENTS

| 3,630,194 | 12/1971 | Boardman | 128/90 |
| 3,814,717 | 6/1974 | Wilson et al. | 260/42.43 |

FOREIGN PATENT DOCUMENTS

| 1,139,430 | 1/1969 | United Kingdom. |
| 831,757 | 3/1960 | United Kingdom. |
| 834,063 | 5/1960 | United Kingdom. |

*Primary Examiner*—James J. Bell
*Attorney, Agent, or Firm*—Jacobs & Jacobs

[57] ABSTRACT

A water-hardenable sheet material comprising a flexible web having deposited thereon an intimate mixture of a water soluble poly(carboxylic acid) or a precursor thereof and an ion leachable inorganic particulate material.

37 Claims, No Drawings

HARDENABLE SHEET MATERIALS

This is a continuation, of Ser. No. 525,731 filed Nov. 21, 1974 now abandoned.

This invention relates to hardenable sheet materials and more particularly to sheet materials which harden on contact with water. Water-hardenable sheet materials have a variety of applications, for example, in orthopaedic surgery they are widely used as splinting materials. Traditionally, bandages comprising plaster-of-Paris are soaked in water and then applied to the affected limb. The plaster-of-Paris hardens within a few minutes to form a rigid casing. Although plaster-of-Paris casts are adequate for some applications, they are heavy, not wholly resistant to water, and partially opaque to x-rays. In addition, plaster-of-Paris casts usually take at least twenty four hours to develop their maximum strength, and this time may be considerably longer in high humidity environments. If a plaster-of-Paris cast is stressed whilst in the "green" state, that is to say before it has reached its maximum strength, it is liable to delaminate, leading to incipient failure of the cast. In some applications these disadvantages can be quite serious, and for this reason many attempts to find an alternative to plaster-of-Paris have been tried. For example, it has been suggested to use a polymerisable resin system which is polymerised by ultraviolet light. However, this requires the use of specialised techniques, and of course involves the expense of a suitable ultraviolet light source. For many surgical applications there is a need for a splinting material which is simple to use, hardens at room temperature without the evolution of substantial amounts of heat, has a high green strength, develops its maximum strength as rapidly as possible, is non-toxic, resistant to hot and cold water, and transparent to x-rays.

In recent years, a range of dental cements have been developed known as the poly(carboxylate) cements and these are described and claimed in British Pat. Nos. 1,139,430 and 1,316,129. These materials normally comprise an ion-leachable powder and an aqueous solution of a poly(carboxylic acid) which when mixed together form a cement of great mechanical strength and water resistance.

The present invention provides a water-hardenable sheet material in which the hardening reaction involves the formation of a poly(carboxylate) cement.

According to the present invention, a water-hardenable sheet material comprises a flexible web having deposited thereon an intimate mixture of a water soluble poly(carboxylic acid) or a precursor thereof and an ion-leachable inorganic particulate material.

The term "sheet" is used in the sense of a body whose breadth is large in comparison with its thickness. The flexible web may be woven, laid down as a non-woven fabric, cast, or extruded. It is preferred that the web be permeable in order to aid the deposition thereon of the water soluble poly(carboxylic acid) or precursor thereof and the ion-leachable inorganic particulate material. For surgical applications, a permeable web has the further advantage that it can allow access of air to the encased limb. The web most preferably has a porous structure, and in the case of woven or non-woven fabrics, the porosity of the web may be conditioned by the method of manufacture, so that this particular characteristic may be predetermined to suit any special requirements.

The flexible web may comprise an organic natural or synthetic polymeric material, and particularly a cellulosic fibrous material such as cotton or other vegetable fibres, animal fibres such as wool, and synthetic polymeric fibrous material such as polyamides, polyesters, and cellulose acetates. The flexible web desirably has sufficient mechanical strength to enable it to act as a reinforcement for the sheet material. For surgical applications very good results have been obtained using a cotton bandage fabric, for example of leno weave. The cotton fibres may be reinforced with glass fibre if desired. Although less preferred, the flexible web may also be in the form of an impermeable film or foil of plastic or other suitable material.

The preferred poly(carboxylate acids) are those prepared by the homopolymerisation and copolymerisation of unsaturated aliphatic carboxylic acids for example acrylic acid, itaconic acid, mesaconic acid, citraconic acid, and aconitic acid, and copolymerisation of these acids with other unsaturated aliphatic monomers, for example, acrylamide and acrylonitrile. Particularly preferred are the homopolymers of acrylic acid, and its copolymers, particularly with itaconic acid.

The preferred copolymers are those prepared by the copolymerisation of acrylic acid with other unsaturated aliphatic carboxylic acid, for example 2-chloro acrylic acid, 3-chloro acrylic acid, 2-bromo acrylic acid, 3-bromo acrylic acid, methacrylic acid, itaconic acid, maleic acid, glutaconic acid, aconitic acid, citraconic acid, mesaconic acid, fumaric acid, and tiglic acid. Other suitable monomers for copolymerising with acrylic acid include unsaturated aliphatic compounds such as for example acrylamide, acrylonitrile, vinyl chloride, allyl chloride, vinyl acetate, and 2-hydroxy ethyl methacrylate. Ter- and higher polymers may be used if desired. Particularly preferred are the copolymers of acrylic acid and itaconic acid. Preferably the mole ratio of acrylic acid to unsaturated aliphatic compound is from 19:1 to 2:1.

The acrylic acid copolymer solution may be prepared by polymerising the appropriate monomers in aqueous solution in the presence of a free radical initiator, for example, ammonium persulphate and various chain transfer agents, for example, isopropyl alcohol to give a solution containing up to about 30% by weight of the copolymer. Such a solution may then be concentrated, if necessary. The copolymer solutions of this invention are preferably prepared by polymerising the monomers in boiling water, that is to say at temperatures at or around 100° C, and particularly at temperatures of from 90° to 100° C. These temperatures are considerably higher than those customarily used in conventional aqueous polymerisation techniques.

Good results have also been obtained using a copolymer of vinyl methyl ether and maleic acid. Any suitable route may be used for the preparation of the poly(carboxylic acid) and for example, polyacrylic acid may be prepared by hydrolysis of polyacrylonitrile. It is also possible to use a precursor of a poly(carboxylic acid) which will be transformed into the poly(carboxylic acid) on contact with water, for example, a poly(carboxylic acid anhydride) or other suitable polymer. The poly(carboxylic acid anhydride) may be a homopolymer of an unsaturated carboxylic acid anhydride, or a copolymer with a vinyl monomer, and particularly a vinyl hydrocarbon monomer. Particularly good results may be obtained using homopolymers of maleic anhydride, and copolymers thereof with ethylene, propene, butene and styrene.

The poly(carboxylic acid) or percursor thereof is preferably linear, although branched polymers may also be used, and preferably has an average molecular weight of from 1,000 to 1,000,000 and most preferably from 10,000 to 100,000. In this specification the average molecular weight is defined as being that measured by gel permeation chromatography.

The poly(carboxylic acid) is preferably in fine particulate form, and most preferably with a degree of fineness such that it will pass through a 150 BS mesh sieve.

The ion-leachable inorganic particulate material may for example comprise a di- or polyvalent metal oxide, preferably one that has been deactivated, for example by heat treatment as described in British Pat. No. 1139430, or by partially coating the surface of the metal oxide particles with an organic acid such as stearic acid. A preferred metal oxide is zinc oxide, to which there may be added up to about 10% by weight of other metal oxides such as, for example magnesium oxide. The di- or polyvalent metal oxide may if desired be replaced by a salt of the di- or polyvalent metal with a weak acid, the weak acid being capable of an exchange reaction with the poly(carboxylic acid) used, for example zinc oxide may be wholly or partially replaced by zinc borate. Alternatively, the ion-leachable inorganic particulate material may comprise a fused oxide made by heating a mixture of simple oxides to fusion temperature or an oxide glass, for example a glass comprising calcium or sodium oxide with alumina and silica. The preferred ion-leachable inorganic materials for use in the present invention are aluminosilicate glasses, wherein the ratio by weight of acidic to basic oxides in the glass is such that the glass will react with a poly(carboxylate acid) in the presence of water to produce a poly(carboxylate) cement. It has been found that the rate of reaction increases with increasing basicity of the aluminosilicate glass and thus the ratio of the oxides in the glass composition can be chosen in order to allow adequate working time to form the water-hardenable sheet material into a desired shape before it has set. For many applications it is preferable to attain a working time of about 5 minutes, or less, and then to have the shortest possible setting time in which the sheet material hardens and attains an appreciable rigidity and mechanical strength. Suitable aluminosilicate glasses may, for example, be prepared by fusing mixtures of alumina, silica, and calcium oxide in the appropriate proportions, together with, if necessary, up to 30% by weight, based on the total weight of the composition, of a flux which may be a fluoride, a borate, a phosphate, or a carbonate.

In this specification the glass compositions are described in the conventional manner as containing alumina, silica, calcium oxide, sodium oxide and other oxides though it is to be understood that these oxides are chemically combined in the matrix of the aluminosilicate glass, and are not present as free oxides. The proportions of oxides quoted for the glass compositions refer to the amounts of these oxides (added in some cases as the corresponding carbonates) added to the glass frit.

The weight ratio of the acidic oxides to basic oxides in the aluminosilicate glass is usually chosen such that the poly(carboxylate) cement stiffens within a relatively short period, termed the working time, which is usually less than ten minutes. It has been found that the rate of reaction increased with increasing basicity of the glass and thus the ratio of the oxides can be chosen in order to allow adequate working time to form the cement into a desired shape before it is has set. For many applications it is preferred to attain a working time of about five minutes, or less, and then to have the shortest possible setting time in which the set cement hardens and attains an appreciable compressive strength. Preferably the ratio by weight of acidic to basic oxides in the glass is from 0.1 to 3.0 and most preferably from 0.2 to 2.5.

The principal acidic oxide in the aluminosilicate glass is silica, although the glass may also contain minor amounts of phosphorus pentoxide, and boric oxide. The principal basic oxide in the glass is alumina, which, although it has amphoteric properties, can be considered for the purposes of the present specification solely as a basic oxide. Particularly preferred aluminosilicate glasses fall within the composition range of 10 to 65% w/w silica, and 15 to 50% w/w alumina.

The aluminosilicate glass desirably contains at least one other basic oxide, preferably calcium oxide, which may be present in the glass composition in an amount of from 0 to 50% w/w. The calcium oxide may be partly or wholly replaced by sodium oxide or another basic oxide or mixture of basic oxides, although in some applications the presence of sodium oxide may be undesirable as this oxide tends to increase the solubility of the resultant cement.

Preferred glasses for use in the present invention containing alumina, silica and calcium oxide are the gehlenite and anorthite glasses, and in general glasses falling within the composition range to 10 to 65% w/w silica, 15 to 50% w/w alumina and 0 to 50% w/w calcium oxide. Certain of the glasses within this general range, more particularly those having a weight ratio of calcium oxide to silica greater than 0.92 or having a weight ratio of calcium oxide to alumina less than 0.74 are new materials and are accordingly included within the invention.

The aluminosilicate glasses of the present invention may be prepared by fusing mixtures of the components in the appropriate proportions at temperatures above 900° C and preferably in the range of 1050° C to 1550° C. The mixture is preferably fused for from 1 to 4 hours. Silica and alumina may be included in the mixture as oxides, but it is convenient to add calcium oxide and sodium oxide as calcium carbonate and sodium carbonate respectively, and references to the presence of these oxides in the glass fusion mixture includes the possibility that they may be added as carbonates or as other compounds which decompose similarly under glass fusion conditions to give the oxides.

The addition of carbonates to the fusion mixture lowers the fusion temperature and thus these can be considered as fluxing agents. If desired, however, the mixture may contain an additional fluxing agent, and this has been found to be important with glass compositions containing less than 10% w/w of calcium oxide. In this connection fluorides such as fluorite and cryolite have been found to be especially useful as fluxing agents, although as previously mentioned it is desirable not to use large amounts of fluorides in the fusion mixture. Accordingly the amount of fluorine in the composition is preferably less than 14% by weight, most preferably less than 8% by weight, based on the total weight of the composition. It has been found that very good results may be obtained using fluorite ($CaF_2$) as a fluxing agent in an amount such that the fluorite is less than 15%, or greater than 90%, on a molar basis, of the total amount of fluorite and calcium oxide present in the glass composition. Other fluxing agents, for example calcium phosphate and aluminium phosphate may also be used, though these are less preferred. The total amount of fluxing agents present in the mixture, including carbonates, may be up to 50% by weight, based on the total weight of the mixture.

After fusion the glass may be poured off and cooled rapidly, for example, in air or water or some combination of both. To a first approximation the proportions of the different elements in the glass may be taken as the proportions of the same elements present in the mixture. Some fluorine may, however, be lost from a fluoride fluxing agent during the reaction.

The glasses used in the present invention may be readily obtained in fine powder form. The degree of fineness of the powder should preferably be such that it produces a smooth cement paste which sets within an acceptable period when mixed with the poly(carboxylic acid) in the presence of water. Preferably the degree of fineness of the powder is such that it will pass through a 150 mesh B.S. sieve and most preferably such that it will pass through a 350 mesh B.S. sieve. Mixtures of different glasses may be used if desired. Most preferably, however, the ion-leachable inorganic particulate material comprises a fluoroaluminosilicate glass, for example as described and claimed in British Pat. No. 1,316,129, wherein the ratio by weight of silica to alumina is from 1.5 to 2.0 and the ratio by weight of fluorine to alumina is from 0.6 to 2.5 or wherein the ratio by weight of silica to alumina is from 0.5 to 1.5 and the ratio by weight of fluorine to alumina is from 0.25 to 2.0. The fluoroaluminosilicate glasses may be prepared by fusing mixtures of silica, alumina, cryolite, and fluorite in the appropriate proportions at a temperature above 950° C. Suitable methods for preparing the glasses are described in the aforementioned British Patent.

The degree of fineness of the ion-leachable inorganic particulate material should preferably be such that when the water-hardenable sheet material is contacted with water it sets in the desired shape within an acceptable period. Preferably the degree of fineness of the ion-leachable inorganic particulate material is such that it will pass through a 150 mesh B.S. sieve and most preferably such that it will pass through a 350 mesh B.S. sieve. Where the ion-leachable inorganic material comprises an aluminosilicate glass, this may be used in the form of glass fibres if desired.

In a preferred method of preparing the water-hardenable sheet materials of this invention, the ion-leachable inorganic particulate material is slurried in a dispersion or solution of the poly(carboxylic acid) or precursor thereof in a suitable organic solvent, for example methyl ethyl ketone, cyclohexanone or methylene dichloride. The flexible web is then impregnated with the slurry by a coating technique, and the organic solvent removed, for example by evaporation. The amount of slurry deposited on the flexible web may be varied within wide limits, but preferably the deposited ion-leachable inorganic particulate material and poly(carboxylic acid) or precursor thereof comprise from about 5 to about 95% by weight, preferably from 60 to 90% by weight, of the total weight of the water-hardenable sheet material. The acid and the ion-leachable inorganic particulate material are preferably present in the ratio of 1 to 100 parts by weight of ion-leachable inorganic particulate material for each 10 parts by weight of the poly(carboxylic acid) or precursor thereof.

Preferably, the slurry comprises a binder to assist the adherence of the ion-leachable inorganic particulate material to the flexible web. Suitable binders include polyvinyl alcohol, polyvinyl acetate and partially hydrolysed polyvinylacetate. Usually only small quantities of the binder are required, for example up to about 5% by weight based on the combined weight of the acid and the inorganic material, and preferably from 0.1 to 1%.

The water-hardenable sheet material may comprise additional components, for example chemically unreactive particulate fillers may be included to effectively eliminate any slight contraction which may take place on hardening of the hardenable sheet material. The particulate inert filler may be selected from a wide range of suitable inorganic and organic materials, but it is preferred to use materials having good packing properties and high compressive strength such as for example sand, talc, and fibrous materials such as asbestos and nylon fibres. Ion leachable cement powders for poly(carboxylate) cements are usually ground to size, thus producing a collection of irregular particles having poor packing properties. Although the invention is not limited to any particular theory, it is believed that the most suitable fillers are those of regular shape which help to minimise the poor packing properties of the cement powder. Preferably the particle size of the inert filler is less than 100 B.S. mesh, and most preferably from 100 to 300 B.S. mesh such as for example about 150 mesh. Very good results have been obtained using graded sand of particle size 100 to 200 B.S. mesh. The inert filler should be substantially unreactive under the reaction conditions, but is preferably a material to which the poly(carboxylate) cement will adhere. The particulate inert filler may be separate from or included in any of the components of the cement pack and is preferably present in an amount of from 10 to 65% by weight, and most preferably from 25 to 50% by weight, based on the total weight of the components.

It is also often found advantageous to add a water soluble chelating agent such as tartaric acid to the water-hardenable sheet material as this has been found to decrease the setting time of poly(carboxylate) cements and increase the strength of the set cement. The chelating agent is added to the poly(carboxylic acid) in an amount sufficient to obtain the desired working time and hardening rate. It is usually not necessary to add more than about 20% by weight of the chelating agent based upon the weight of the poly(carboxylic acid) and preferably the chelating agent is present in an amount of from 0.01 to 10% by weight, such as for example about 5% by weight, based on the weight of the poly(carboxylic acid). A wide range of chelating agents may be used in the present invention, particularly those containing chelating hydroxy or carboxyl groups or both, such as for example, ethylene diamine tetraacetic acid, salicylic acid, citric acid, 2,4 and 2,6-dihydroxybenzoic acids, dihydroxy tartaric acid, nitrilotriacetic acid, tartaric acid, mellitic acids and polyglycols. Excellent results have been obtained using 5% by weight of tartaric or citric acid. Alternatively, the chelating agent may be added in the form of a metal chelate, particularly a di- or tri-valent metal chelate. Examples of especially suitable metal chelates include complexes of $\beta$-diketones with aluminium and chromium, for example aluminium and chromium triacetylacetonates, and ethylene diamine tetraacetic acid complexes of zinc and copper.

In low humidity environments, poly(carboxylate) cements tend to lose water and this may have a slight detrimental effect upon the strength of the hardened sheet material. This effect may be substantially overcome by including in the slurry to be applied to the flexible web a water insoluble polymer. Such a polymer may, for example, be dissolved or emulsified in the organic solvent so that after removal of the solvent the water insoluble polymer is in particulate form, intimately mixed with the other components. The water insoluble polymer preferably comprises pendant carboxylic acid groups which can take part in the hardening reaction, and for example it may comprise a copolymer of an unsaturated aliphatic carboxylic acid for example acrylic acid, methacrylic acid and itaconic acid, and an unsaturated aliphatic ester, for example an acrylic ester such as methyl methacrylate, ethyl acrylate and ethyl methacrylate. Good results may be obtained using a copolymer of methacrylic acid and ethyl acrylate. Alternatively the water insoluble polymer may be applied to the water-hardenable sheet material as an aqueous emulsion at the time of use.

When used as splinting materials, the water-hardenable sheet materials of this invention are designed to be used by the practitioner in the same manner as the conventional plaster-of-Paris splinting materials. Thus the water-hardenable sheet material in the form of a roll may be contacted with water by, for example, dipping or spraying, and then wound around the limb which it is desired to encase, overlapping adjacent turns as required. The sheet material is initially flexible enabling it to be formed into a desired shape prior to hardening. Within a relatively short time, usually a few minutes, however, the hardening has proceeded to an extent sufficient to produce a hard tough cast. The hardening reaction may be accelerated by the use of warm water.

The water-hardenable sheet materials of the present invention may also find applications outside conventional surgical use, for example they may be used in forestry to repair damaged branches of young trees, and may find application as modelling materials for children.

The invention is illustrated by the following Examples:

EXAMPLE 1

This Example describes the production of a water-hardenable sheet material according to the present invention and its application to the manufacture of surgical splints.

80.0 gms. of a fluroaluminosilicate glass powder prepared as described in Example 2 of British Pat. No. 1,316,129 and having a particle size of 350 B.S. mesh are intimately mixed with 24.4 gms. of finely powdered polyacrylic acid of average molecular weight 90000 and water content 8% by weight. This mixture is slurried in methylethyl ketone to give a suspension of about 40% solids, and 0.5 gm. of poly(vinyl acetate) binder added. With the suspension in agitation, 50 mm width leno gauze bandage is passed through and the pick-up of solids controlled with a doctor blade. The methylethylketone is removed by drying under a hot air blower whereupon the gauze can be rolled up in the manner of a conventional bandage.

The coated gauze is then sprayed with water, and wound around a cylindrical mandrel, smoothing the turns by hand. The turns of the gauze are allowed to overlap so that on hardening, after 30 minutes, the gauze can be removed from the mandrel as a hollow cylindrical cast. After 48 hours the cast is cut up into rings, mounted in an Instron machine and subjected to compression at a rate of 5 mm.min$^{-1}$. The stresses for strains of 5%, 10% and 12.5% are calculated. For the purposes of comparison, a plaster-of-Paris cast is prepared in the same manner and similarly tested for compressive strength. The results are given below:

TABLE 1:

| Specimen Ring Dimensions | Poly(carboxylate) | Plaster-of-Paris |
|---|---|---|
| Length (mm) | 15 | 15 |
| Internal diameter (mm) | 14 | 14 |
| External Diameter (mm) | 15.5 | 18 |
| Weight of material (Kgm$^{-2}$) | 0.183 | 0.398 |
| Length of gauze bandage (mm) | 225 | 225 |

TABLE 2:

| | Average Stress (N) | |
|---|---|---|
| Strain (%) | Poly(carboxylate) | Plaster-of-Paris |
| 5 | 16.3 | 21.1 |
| 10 | 22.4 | 26.4 |
| 12.5 | 24.2 | 28.8 |

These results show that the water-hardenable sheet materials of the present invention have excellent compressive strength combined with a considerable reduction in weight. Although the poly(carboxylate) cast is half the weight of the plaster-of-Paris cast, its compressive strength is only slightly less. In addition, the poly(carboxylate) cast is not attacked by hot or cold water, is non-toxic and non-irritational, and is transparent to x-rays. The average time taken for a poly(carboxylate) cast to reach its maximum strength is about 8 hours, in comparison with 24 hours for a plaster-of-Paris cast.

Further tensile stress tests carried out on samples of comparable size show that a poly(carboxylate) cast is almost twice as strong as a cast made from plaster-of-Paris.

Examples 2–4 illustrate the preparation of suitable aluminosilicate glasses.

EXAMPLE 2

A series of glasses are prepared by fusing mixtures of silica, alumina, calcium and sodium carbonates as set out in Table 1 below in a platinum crucible. After fusion the glass is poured off and cooled rapidly. The glass compositions and fusion conditions are as follows:

Table 3

| | I | II | III |
|---|---|---|---|
| $SiO_2$ | 118 | 143 | 118 |
| $Al_2O_3$ | 100 | 100 | 100 |
| CaO* | 110 | 32 | 55 |
| $Na_2O$* | — | 20 | — |
| Fusion temperature (° C) | 1400 | 1500 | 1550 |
| Time (hours) | 2¼ | 3¾ | 1 |

*added as carbonates to the fusion mixture.

The resultant glasses are dried and crushed until they pass through a 350 mesh B.S. sieve.

EXAMPLE 3

The following compounds are mixed by milling and then heated in a sillimanite crucible at 1250° C until homogeneous (about 3 hours).

| Silica | 143 gms. |
|---|---|
| Alumina | 100 gms. |
| Cryolite | 76 gms. |

-continued

| | |
|---|---|
| Fluorite | 56 gms. |
| Aluminium phosphate | 73 gms. |

The glass is prepared as described in Example 2 and crushed until it passes through a 350 mesh B.S. sieve. The glass is found to have a fluorine content of about 13.5% by weight (determined by the method of A. C. D. Newman in 'Analyst', 1968 vol. 93 page 827).

EXAMPLE 4

A series of glasses are prepared by fusing mixtures of compounds in amounts and at fusion conditions as listed in Table 4:

TABLE 4

| | A | B | C | D | E | F | G | H | I |
|---|---|---|---|---|---|---|---|---|---|
| $SiO_2$ | 180 gms | 60 gms | 120 gms | 240 gms | 87 gms | 286 gms | 120 gms | 240 gms | 120 gms |
| $Al_2O_3$ | 102 gms | 102 gms | 102 gms | 102 gms | 102 gms | 200 gms | 102 gms | 102 gms | 102 gms |
| CaO* | 56 gms | 112 gms | 93 gms | 168 gms | 78 gms | 64 gms | 168 gms | 112 gms | 101 gms |
| $Na_2O$* | | | | | | 39 gms | | | |
| $CaF_2$ | | | 26 gms | | | | | | 156 gms |
| Fusion temperature (° C) | 1500–1550 | 1400–1550 | 1450 | 1450 | 1430 | 1400–1500 | 1525 | 1430–1500 | 1450 |
| Time | 4 hrs | 85 min | 90 min | 90 min | 90 min | 2¼ hrs | 85 min | 2 hrs | 90 min |

*added as carbonates to the fusion mixture

The resultant glasses are dried and crushed until they pass through a 350 mesh B.S. sieve.

Examples 5 and 6 illustrate the preparation of acrylic copolymers.

EXAMPLE 5

This Example describes the preparation of a poly(carboxylate) cement using as the cement-forming liquid an aqueous solution of a 1:4 mole ratio copolymer of itaconic acid and acrylic acid. 2.5 parts by weight of ammonium persulphate and 200 parts by volume of water are placed in a three-necked round bottomed flask fitted with a condenser, and nitrogen is bubbled through the solution.

Solution A is 72.3 parts by weight of acrylic acid, 20 parts by volume of propan-2-ol and 100 parts by volume of water. Solution B is 2.5 parts by weight of ammonium persulphate and 60 parts by volume of water. 32.7 parts by weight of itaconic acid is divided into 24 equal parts. The solution in the flask is heated to boiling and additions of solutions A and B and itaconic acid are made at approximately 5 minute intervals. After the completion of the additions the solution is heated for a further two hours. The reaction product is concentrated to 50% w/w concentration by vacuum distillation at 40°–45°.

There is produced an aqueous solution of an acrylic acid/itaconic acid copolymer having a molecular weight of 18,000 and a viscosity of 26 poise.

EXAMPLE 6

This Example describes the preparation of a poly(carboxylate) cement using as the cement-forming liquid an aqueous solution of a 1:2 mole ratio copolymer of itaconic acid and acrylic acid.

The procedure of Example 5 is repeated using 55.7 parts by weight of acrylic acid and 49.8 parts by weight of itaconic acid. There is obtained a 50% w/w aqueous solution of an acrylic acid/itaconic acid copolymer containing 47.4% itaconic acid units, having a molecular weight of 10,000 and a viscosity of 11 poise.

Examples 7 and 8 illustrate the use of the inert filler.

EXAMPLE 7

The following components are mixed by milling and then heated at 1100° C for 1½ hours.

| | |
|---|---|
| $SiO_2$ | 333 g |
| $Al_2O_3$ | 128 g |
| $CaF_2$ | 217 g |
| $Na_3AlF_6$ | 194 g |
| $AlPO_4$ | 136 g |
| $AlF_3$ | 31 g |

The resultant glass is cooled rapidly, dried, and crushed until it passes through a 350 mesh B.S. sieve.

Mixtures of the glass powder are made up in various proportions with fine sand (Redhill AFS 80) of particle size from 100 to 200 B.S. mesh and a liquid that is either a 47.3% w/w aqueous polyacrylic acid solution or a 28% w/w aqueous ethylene-maleic acid (1:1) copolymer solution. All mixes are spatulated for 1 to 2 minutes and then placed in a hole 6.4 × 25.4 (diameter) mm in a wooden block. After levelling the cement mix the samples are aged for five days under ambient conditions. After ageing the condition of the cement is noted and the shrinkage measured by a depth gauge positioned at the centre of the cement surface. The results are giving in Table 5 in which G represents glass powder, P represents polyacrylic acid solution, E represents ethylene-maleic acid copolymer solution and S represents sand.

TABLE 5

| | MIX PROPERTIES | | | SET CEMENT PROPERTIES | |
|---|---|---|---|---|---|
| Sample No. | Composition (parts by weight) | State of mix | Workability | Shrinkage (mm) | State of cement |
| 1 | 1G+1P | Very sticky, thin mix. | Fairly difficult to use. | 2.4 | Fine cracks |
| 2 | 2G+1P | Extremely sticky. Stiff mix. | Difficult to use. | 0.8 | Fine cracks |
| 3 | 3G+1P | Extremely sticky. Very stiff. | Very difficult to use. | 0.4 | Very fine cracks |
| 4 | 1G+1E | Very fluid. Not sticky. | Pourable | 3.0 | Split with huge cracks |

TABLE 5-continued

| Sample No. | Composition (parts by weight) | MIX PROPERTIES State of mix | Workability | SET CEMENT PROPERTIES Shrinkage (mm) | State of cement |
|---|---|---|---|---|---|
| 5 | 2G+1E | Fairly fluid Not sticky. | Fairly pourable | 1.6 | Large cracks |
| 6 | 3G+1E | Quite fluid. Not too sticky | Easy to use | 0.4 | Cracked |
| 7 | 1G+1P+1S | Fluid mix. Rather sticky. | Quite easy to use. | 1.6 | No cracks |
| 8 | 2G+1P+2S | Doughy, quite stiff. Not too sticky. | Very good to use. | 0.6 | No cracks |
| 9 | 1G+1P+2S | Fairly stiff. Not too sticky | Easy to use | 1.2 | No cracks |
| 10 | 1G+1P+3S | Doughy, stiff mix. Not very sticky. | Very good to use. | 0.6 | No cracks |
| 11 | 1G+1E+1S | Very fluid. Not too sticky. | Pourable | 1.8 | Cracked |
| 12 | 2G+1E+1S | Fluid mix. | Fairly easy to use. | 0.6 | No cracks |
| 13 | 3G+1E+3S | Doughy, stiff mix. | Very good to use. | 0.0 | No cracks |
| 14 | 1G+1E+3S | Fairly fluid | Fairly easy to use. | 0.8 | No cracks |
| 15 | 2G+1E+3S | Doughy, very stiff. Not sticky. | Extremely easy to use. | 0.0 | No cracks |

These results show that the addition of an inert filler decreases the stickiness of the mix and thus improves its workability, and decreases shrinkage and the tendency for cracks to appear in the set cement.

EXAMPLE 8

The procedure of Example 7 is repeated replacing the sand with asbestos type M2(7-M) manufactured by Central Asbestos Co. Ltd. The result is as follows:

| Sample No. | Composition (by wt) | State of mix | Workability | Shrinkage mm. | State of cement |
|---|---|---|---|---|---|
| 16 | 4G + 1A* + 1P | Fairly stiff | Fair | 0.5 | No cracks |

A represents asbestos type M2(7-M) ex Central Asbestos Co. Ltd.

Examples 9-11 illustrate the use of a chelating agent.

EXAMPLE 9

This example describes the production of a poly(carboxylate) dental cement from a fluoroaluminosilicate glass powder, and an aqueous solution of poly(acrylic acid) containing tartaric acid as a chelating agent.

The fluoroaluminosilicate glass powder is made by mixing together 175 parts by weight of silica, 100 parts by weight of alumina, 30 parts by weight of cryolite, 207 parts by weight of calcium fluoride, 32 parts by weight of aluminium fluoride, and 60 parts by weight of aluminium phosphate, and heating to a temperature of 1150° C. The glass is ground to a mesh size of 350 BSS mesh. The aqueous poly(acrylic acid) solution contains 50% by weight of a poly(acrylic acid) of average molecular weight 28,000 and 5% based on the weight of the poly(acrylic acid) of tartaric acid. The powder and the liquid are mixed together in the ratio of 3.5 gms. of powder to 1 milliliter of liquid. Hardness of the cement is measured by indentation 9 minutes after mixing. For comparison a sample of the powder is mixed with an identical poly(acrylic acid) solution except that the tartaric acid is omitted, in a powder to liquid ratio of 3 gms. of powder to 1 milliliter of liquid, giving a cement of the same consistency as the previous cement containing the chelating agent. The results of setting time, working time, and hardness of the two cements are given below:

|  | With Tartaric acid | Without tartaric acid |
|---|---|---|
| Setting time (min) | 3¼ | 6 |
| Working time (min) | 2 | 2½ |
| Wallace Indentation Number at 9 mins. | 120 | 600 |

EXAMPLE 10

This example describes the production of a poly(carboxylate) dental cement using a fluoroaluminosilicate glass powder and an aqueous solution of poly(acrylic acid) containing citric acid as a chelating agent.

The procedure of Example 9 is repeated except that the tartaric acid is replaced by 5% by weight of the poly(acrylic acid) of citric acid. The results of this cement are given below:

| Setting time | 3¾ mins |
|---|---|
| Working time | 2 mins |
| Wallace Indentation Number at 9 mins | 347 |

EXAMPLE 11

This example describes the production of a poly(carboxylate) dental cement using a fluoroaluminosilicate glass powder and an aqueous solution of poly(acrylic acid) containing tartaric acid as a chelating agent and propan-2-ol as a stabilising agent.

The procedure of Example 9 is repeated except that the liquid contains in addition to the tartaric acid, 5%, based on the weight of the poly(acrylic acid) of propan-2-ol. The results for this cement are given below:

| Setting time (min) | 3½ |
|---|---|
| Working time (min) | 2 |
| Wallace Indentation Number 9 mins | 120 |

We claim:

1. A water-hardenable sheet useful as a splinting material for portions of the human and animal anatomy which comprises a flexible web having adhered thereto a cement-forming material, said cement-forming material comprising a water-soluble poly(carboxylic acid) or a precursor thereof that forms a poly(carboxylic acid) on contact with water and an ion-leachable inorganic particulate material, which together form a cement upon contact with water, said cement-forming material being present in an amount sufficient to form a splinting material for portions of the human or animal anatomy upon the addition of the amount of water necessary to harden said sheet.

2. A water-hardenable sheet according to claim 1 in which the flexible web has a porous structure.

3. A water-hardenable sheet according to claim 1 in which the flexible web comprises a cellulosic fibrous material.

4. A water-hardenable sheet according to claim 1 in which the poly(carboxylic acid) is a homopolymer or copolymer of acrylic acid.

5. A water-hardenable sheet according to claim 1 in which the precursor is a poly(carboxylic acid anhydride).

6. A water-hardenable sheet according to claim 1 in which the poly(carboxylic acid) or precursor thereof has an average molecular weight of from 10,000 to 100,000.

7. A water-hardenable sheet according to claim 1 in which the poly(carboxylic acid) or precursor thereof is in particulate form, and has a degree of fineness such that it will pass through a 150 B.S. mesh sieve.

8. A water-hardenable sheet according to claim 1 in which the ion-leachable inorganic particulate material is an oxide of a di- or poly-valent metal, or a salt of a weak acid and a di- or poly-valent metal.

9. A water-hardenable sheet according to claim 8, in which the oxide is zinc oxide.

10. A water-hardenable sheet according to claim 1 in which the ion-leachable inorganic particulate material is an aluminosilicate glass.

11. A water-hardenable sheet according to claim 10, in which the aluminosilicate glass has been prepared by fusing a mixture of alumina, silica, and calcium oxide together with up to 30% by weight, based on the total weight of the composition, of a fluoride, borate, phosphate, or carbonate flux.

12. A water-hardenable sheet according to claim 10, in which the aluminosilicate glass is a fluoroaluminosilicate glass.

13. A water-hardenable sheet according to claim 1 in which the ion-leachable inorganic particulate material has a degree of fineness such that it will pass through a 150 mesh B.S. sieve.

14. A water-hardenable sheet according to claim 1 in which the weight of the cement-forming material is from 60 to 90% of the total weight of the flexible web and the cement-forming material.

15. A water-hardenable sheet according to claim 14, in which the poly(carboxylic acid) or precursor thereof and the ion-leachable inorganic particulate material are present in the ratio of 1 to 100 parts by weight of ion-leachable inorganic particulate material to every 10 parts by weight of the poly(carboxylic acid) or precursor thereof.

16. A water-hardenable sheet according to claim 1 which further comprises a binder to assist the adherence of the ion-leachable inorganic particulate material to the flexible web.

17. A water-hardenable sheet according to claim 16, in which the binder is polyvinyl alcohol, polyvinyl acetate, or partially hydrolysed polyvinyl acetate.

18. A water-hardenable sheet according to claim 16, in which the binder is present in an amount of from 0.1 to 1% by weight based on the combined weight of the acid and the inorganic material.

19. A water-hardenable sheet according to claim 1 which further comprises an anti-shrinkage agent.

20. A water-hardenable sheet according to claim 19 in which said anti-shrinkage agent is an inert particulate filler.

21. A water-hardenable sheet according to claim 1 which further comprises a water soluble chelating agent.

22. A water-hardenable sheet according to claim 1 which further comprises a water insoluble polymer in particulate form.

23. A water-hardenable sheet according to claim 22, in which the water insoluble polymer has pendant carboxylic acid groups.

24. A water-hardenable sheet material according to claim 22 in which the water insoluble polymer is a copolymer of an unsaturated aliphatic carboxylic acid and an unsaturated aliphatic ester.

25. A water-hardenable sheet according to claim 22 in which the water insoluble polymer is a copolymer of methacrylic acid and ethyl acrylate.

26. A water-hardenable sheet according to claim 10, wherein said aluminosilicate glass has been prepared by fusing a mixture of 10 to 65% silica, 15 to 50% alumina, 0 to 50% calcium oxide and a fluorine-containing fluxing agent to provide fluorine in an amount of less than 14%, based on the weight of the composition.

27. A water-hardenable sheet according to claim 10, wherein the amount of fluorine is less than 8%.

28. A water-hardenable sheet according to claim 27 wherein the aluminosilicate glass has a degree of fineness such that it will pass through a 150 mesh B.S. screen.

29. A water-hardenable sheet according to claim 1 wherein said poly(carboxylic acid) is a copolymer of vinyl methyl ether and maleic anhydride.

30. A water-hardenable sheet according to claim 1 wherein the ion-leachable inorganic particulate material is a powder selected from the group consisting of an oxide of a di- or poly-valent metal, a salt of a weak acid and a di- or poly-valent metal and an aluminosilicate glass, and the weight of the cement-forming material is from about 5 to 95% by weight of the flexible web and the cement-forming material.

31. A water-hardenable sheet according to claim 30 in which the ion-leachable inorganic particulate powder is a fluoroaluminosilicate glass.

32. A water-hardenable sheet according to claim 30 in which the weight of the cement-forming material is from 60 to 90% of the total weight of the flexible web and the cement-forming material.

33. A water-hardenable sheet according to claim 32 in which the poly(carboxylic acid) or precursor thereof and the ion-leachable inorganic particulate powder are present in the ratio of 1 to 100 parts by weight of ion-leachable inorganic particulate powder to every 10 parts by weight of the poly(carboxylic acid) or precursor thereof.

34. A water-hardenable sheet according to claim 30, in which the poly(carboxylic acid) is a homopolymer or copolymer of acrylic acid.

35. A water-hardenable sheet according to claim 34 in which the poly(carboxylic acid) has an average molecular weight of from 10,000 to 100,000.

36. A substantially rigid sheet material comprising a flexible web and a poly(carboxylate) cement in layered relationship, the poly(carboxylate) cement having been formed by reaction in the presence of water of a water-soluble poly(carboxylic acid) or a precursor thereof that will be transformed into the poly(carboxylic acid) on contact with water, and an ion-leachable inorganic particulate cement-forming material.

37. A process for the production of a water-hardenable sheet material, which comprises depositing on to a flexible web reactants that react together in the presence of water to form a poly(carboxylate) cement, said reactants being a water soluble poly(carboxylic acid) or a precursor thereof that will be transformed into the poly(carboxylic acid) on contact with water and an ion-leachable inorganic particulate cement-forming material.

* * * * *